(12) United States Patent
Kelly et al.

(10) Patent No.: US 6,355,467 B1
(45) Date of Patent: Mar. 12, 2002

(54) SACCHARIFICATION ENZYMES FROM HYPERTHERMOPHILIC BACTERIA AND PROCESSES FOR THEIR PRODUCTION

(75) Inventors: Robert M. Kelly, Ellicott City; Stephen H. Brown, Owings Mills, both of MD (US); Henry R. Costantino, Westfield, NJ (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/503,335

(22) Filed: Feb. 14, 2000

Related U.S. Application Data (62) Division of application No. 07/424,170, filed on Oct. 20, 1989, now abandoned.

(51) Int. Cl.$^7$ .............................. C12N 9/28; C12N 9/24
(52) U.S. Cl. ........................ 435/202; 435/200; 435/201
(58) Field of Search ............................... 435/202, 200, 435/201

(56) References Cited

U.S. PATENT DOCUMENTS 5,023,094 A    6/1991    Van Eyk .................. 426/20

OTHER PUBLICATIONS

Khoo et al. "Interactions of calcium and other metal ions with caldolysin, ther thermostable proteinase from Thermus aquatics strain T351", Biochem. J. (1984) 221, 407–413.
DSM Catalogue of Strains 1989, pp. I–Viii; p. 97—Pyrococcus Furiosus Stetter and Fiala 1986; Archaebacterium, Representing a Novel Order, Therococcales, System Appl. Micro biol. 9, 62–70 (1987).
Zillig et al., Pyrococcus woesei, sp. nov., an Ultra–Thermophilic Marine Archaebacterium, Representing a Novel Order, thermococcales, System Appl. Micro biol. 9, 62–70 (1987).
Matsubara, Methods in Enzymology, Vol. XIX, Protolytic enzymes, 1970 Academic Press, NY, "Purification and Assay of Thermolysin", 642–650.
Stettler, K.O., "Hyperthermophiles—Physiology and Enzymes", J. Chem. Technol Biotechnol., vol. 42, No. 4, pp. 351–317, 1988.
Bragger et al., "Very stable enzymes from extremely thermophilic archaebacteria and eubacteria", vol. 264, No. 9, pp. 5070–5079, 1989.
Antranikian et al., "Production of Thermostable α–Glucosidase in Continuous Culture by a New Clostridium Isolate", Appl. Environment Microbiol., Vol. 53, No. 7, 1987.
Melasniemi, H., "Effect of Carbon Source on Production of Thermostable α–Amylase, Pullulanase and α–Glucosidase by Clostridium thermophydrosulfuricum", J. Gen. Microbiol., vol. 133, pp. 883–890, 1987.

Fiala et al., Pyroccoccus furiosus sp. nov. Represents a Novel Genus of Marine Heterotropic archaebacteria Growing Optimally at 100 C, Microbiology, 5 Springer–Verlag 1986, 56–60.

Bryant et al., "Characterization of Hydrogenase from the Hyperthermophilic Archaebacterium Pyroccoccus furiosus", The Journal of Biological Chemistry, vol. 264, No. 264, No. 9, issue of March 25, pp. 5070–50079.

Ano et al. "A Novel and Remarkably Thermostable Ferrodoxin from the Hyperthermophilic Archaebacterium Pyroccoccus furiosus", Journal of Bacteriology, Jun. 1989, p. 3422–3439, vol. 171, No. 6.

Koch et al. "Extremely Thermostable Amylolytic Enzyme from the Archaebacterium Pyrococcus furiosus", FEMS Microbiology Letters 71, 1990, 21–26.

Kelly et al. "Extremely Thermophilic Archaebacteria: Biological and Engineering Considerations", Biotechnology Progress (vol. 4, No. 2, Jun. 1988, reprinted from Chemical Engineering Progress, Aug. 1988, pp. 47–62.

Parameswaran et al., "Engineering Considerations for Growth of Bacteria at Tekmperatures Around 100 C", The Humana Press Inc., Copyright 1988, pp. 53–73.

Cowan et al., "An extremely thermostable extracellular proteinase from a strain of the archaebacterium Desulfurococcus growing at 88 C", Biochem. J. (1987) 247, 121–133, pp. 121–133.

Matsuzawa et al., Production of Therophilic Extracellular Proteases (Aqualysin I and II) by Thermus Aquatics YT–1, An Extreme Thermophile, Agric. Biol. Chem. 47 (1), 25–28, 1983.

Brown et al., Appl. Env. Microbiol., 1989, 55, 2086–2088.*

Brown et al., Appl. Environm. Microbiol., 1990, vol. 56, pp. 1985–1991.*

Constantino, J. Bacteriol., 1990, vol. 172, pp. 3654–3660.*

Kelly, et al., ACS Symp. Ser. (1992), 498(Biocatal. Extreme Temp.), 23–41.*

\* cited by examiner

Primary Examiner—Irene Marx
(74) Attorney, Agent, or Firm—Venable; Ann S. Hobbs (57) ABSTRACT

It has been found that *Pyrococcus furiosus* produces several starch hydrolyzing enzymes, both extracellularly and intracellularly, which retain their activity for several hours at or above 100° C. These comprise an α-glucosidase, which has been highly purified, and amylolytic enzymes including an amylase and a pullulanase. In addition, at least one thermostable enzyme activity from *P. furiosus* that is useful in the process of degradation of cellulose to D-glucose has also been found, namely a β-glucosidase, which is also active up to at least 95° C.

3 Claims, 8 Drawing Sheets

SACCHARIFICATION ENZYMES FROM HYPERTHERMOPHILIC BACTERIA AND PROCESSES FOR THEIR PRODUCTION

This is a division of application Ser. No. 07/424,170, filed Oct. 20, 1989 now abandoned.

BACKGROUND OF THE INVENTION

The present invention relates to saccharification enzymes (i.e., enzymes that hydrolyze polysaccharides into constituent sugars) obtainable from hyperthermophilic bacteria, and processes for producing them. In particular, this invention relates to the following types of thermostable enzymes: amylases, pullulanases, α-glucosidases and β-glucosidases.

Hyperthermophilic bacteria, i.e. bacteria which thrive on temperatures around the boiling point of water, are found in the depths of the ocean close to geothermal springs. Since these bacteria live in high temperature environments, their enzymes, which are essential to sustaining life processes, such as digestion and respiration, must be able to function at such extreme temperature conditions. Enzymes in common mesophilic bacteria (i.e., organisms that can grow at intermediate temperatures compared to the upper and lower extremes for all organisms) degenerate rapidly at these high temperatures.

Proteins which can function at high temperatures can be extremely advantageous for use in a number of industries. For example, soda syrup, laundry detergent, and many pharmaceuticals contain, or are manufactured by, enzymes extracted from microbes. If enzymes from hyperthermophilic bacteria were used in place of the enzymes commonly used today, the processes to make these products could be performed at higher temperatures. Higher temperatures speed up reactions and prevent contamination by fungi and common bacteria. Alternatively, lesser amounts of the enzymes from hyperthermophilic bacteria might be required to sustain enzymatic processes under current temperature conditions where the thermostability of such enzymes correlates with a longer useful life under those conditions.

A number of microorganisms that are capable of growth at or above 100° C. (i.e., hyperthermophiles) have been isolated from several terrestrial and marine environments and are of considerable scientific interest. (See Kelly, R. M., and J. W. Deming, 1988, "Extremely Thermophilic Archaebacteria: Biological and Engineering Considerations", Chem. Engr. Prog. 4:47–62; and Wiegel J., and L. G. Ljungdahl, 1986, "The Importance of Thermophilic Bacteria In Biotechnology," CRC Crit. Rev. Microbiol. 3:39–107.) However, previously it has not been possible to take full advantage of the utility potential of these organisms, in large part because of a lack of understanding of their growth and metabolic characteristics.

Detailed study of specific enzymes from hyperthermophiles is just beginning, and the few known reports on such enzymes that have been published so far all appeared in 1989. For example, it has been shown (Pihl, T. D. et al., 1989, Proc. Nat. Acad. Sci. 86:138–141) that an extremely thermostable hydrogenase isolated from *Pyrodictium brockii* is immunologically related to the comparable enzyme in the *Bradyrhizobium japonicum,* a mesophile. Adams and coworkers have described several distinctive characteristics of a hydrogenase (Bryant, F. O. and Adams, M. W. W., 1989, J. Biol. Chem. 264:5070–5079) and a ferredoxin (Aono, S., et al., 1989, J. Bacteriol. 171:3433–3439) from the hyperthermophilic bacterium, *Pyrococcus furiosus.*

In the broad context of the present invention, saccharification is the process of degradation of a polysaccharide into its basic constituents which are simple sugars. Complex polysaccharides, such as cellulose (in plant cell walls), chitin (in the outer coverings of insects and crustaceans), glycogen (in animal cells) and starch (in plant cells) are all macromolecular polymers of simple sugars, mainly D-glucose, coupled by various chemical linkages into linear and cross-linked or branched networks. Thus, to degrade such polymeric substrates into their simplest sugar components requires a variety of saccharification enzymes having different specificities with respect to the type of sugar (e.g, five or six carbon ring), the positions of linkages between those sugars [e.g., carbon 1 to carbon 4 (i.e., 1,4 linkage) or 1,6 linkage] and the isomeric configurations of those linkages (e.g., α-1,4 or β-1,4).

Starch, for example, is a highly branched polymer essentially composed of α-D-glucose coupled by both α-1,4- and α-1,6- glycosidic linkages. The current industrial processes of digestion of starch into simple sugars (e.g., in the making of corn syrup sweeteners) illustrate many problems with the enzymes that are presently available for large scale digestion of polysaccharides. Two enzymatic steps are applied in the hydrolysis of starch to α-D-glucose. Although the entire process may be considered saccharification in the broad context of this application, the two steps are commonly known as liquification and saccharification. Liquification involves the use of an α-amylase to hydrolyze starch granules which have been slurried in water and gelatinized by heat to allow the enzyme to attack. This process is designed to reduce the viscosity of the hydrolysate and produce a high yield of low molecular weight polysaccharides, primarily dextrins. In the saccharification step, these dextrins are then further hydrolyzed to glucose by another enzyme activity which may be a classified as a glucoamylase. The commercial objective in the overall starch hydrolysis process is to obtain a hydrolysate with maximum glucose content (DX), at least 96% of the dry weight of starch.

A recent comparison of α-amylases (i.e., 1,4-α-D-glucanohydrolases) that are available for commercial scale starch liquification (Shetty, J. K. and Allen, W. G., 1988, Cereal Foods World 33:929–934) pointed out deficiencies in the industry standard, the *Bacillus licheniformis* α-amylase, even though it does meet present operational and performance demands of starch processors. Areas for improvement include: reducing demands for chemicals, ion exchange processing, and other product refining; reducing by-product and color formation; and improving glucose yield and product quality.

Control of pH is critical to the efficiency and operation of current commercial starch liquification processes. Values of lower than pH 6.2 to 6.4 decrease the reaction rate and the stability of the *Bacillus licheniformis* α-amylase. At higher. pH values, color and by-product formation during liquefaction increase with increasing pH. The pH of the refined starch slurry that enters the enzyme liquefaction process from the wet milling operation is normally in the range of 4.0–5.0. For liquification by the *Bacillus licheniformis* α-amylase, base must be added to increase the pH of the starch slurry to the range of 6.2–6.4. After liquefaction, acid must be added for efficient saccharification, typically by a glucoamylase at pH 4.2–4.5. Therefore, the ability to perform liquefactions at a lower pH would decrease the demand for chemically adjusting pH prior to and after liquefaction. It would also reduce color and by-product formation, and lower refining requirements and costs.

An additional problem with *Bacillus licheniformis* α-amylase is that it is a metalloprotein, requiring calcium ion for maximum stability of the enzymatically active configuration. Calcium binding increases resistance to denaturation at extremes of temperature and pH, but the ion is not involved in the starch hydrolysis reaction. Calcium salts are normally added to starch slurry for enzymatic liquification at, for example, 80 mg calcium ion/kg enzyme. Addition of calcium ion reduces enzyme cost but increases product refining cost. Therefore, a more stable enzyme would reduce the amount of calcium ion that must be added for enzyme stabilization and would thereby reduce costs of its removal later. Further, a more stable enzyme would reduce the required amount of the enzyme itself, under current reaction conditions; or, alternatively, higher temperatures could be used to shorten reaction times.

A principal reason that the starch industry has difficulties in achieving 96% DX is that a major by-product in the current starch-to-glucose processes is maltulose, a disaccharide consisting of an α-1,4-glucosidic linkage between glucose and fructose (4-alpha-glucopyranosyl-D-fructose). Maltulose is formed by a nonenzymatic reaction during starch hydrolysis and is resistant to glucoamylase hydrolysis; and therefore, its formation reduces final glucose yields.

A recent study shows (Shetty, J. K. and Allen, W. G., 1988, supra) that maltulose formation is eliminated when liquifications are carried out below pH 6.0. (e.g., in the range of pH 5.0 to 5.8). In the same study, the stabilities of the four commercially available α-amylases at pH 5.8 and 95° C., the current liquification temperature, were compared. The highest thermostability was exhibited by an α-amylase called TT-II, from a particular strains of $Bacillus\ licheniformis$. Under process conditions except for the absence of substrate, with 10 mg/kg calcium ion, TT-II lost about 10% of its activity in 25 minutes; in the presence of substrate (35% starch and 25 mg/kg added calcium ion), this time was extended to slight over 3 hours. These results imply half-lives at 95° C. of about 2 hours and about 16 hours at 95° C. in the absence or presence of substrate, respectively, for TT-II, the best commercially available α-amylase for starch liquification.

As noted above, the liquification step of starch hydrolysis reduces viscosity of the hydrolysate and produces a high yield of oligosaccharide dextrins and some maltose. In saccharification, these maltodextrins and maltose are then further hydrolyzed to the final product, α-D-glucose, by some other enzyme activity which may be a glucoamylase from some microbial source.

Other polysaccharide degrading enzymes with broad substrate specificity are known, for example, a pullulanase, also known as a debranching enzyme, which attacks α-1,6-glycosidic linkages and can completely hydrolyze various polysaccharides into maltotriose (the microbial polysaccharide pullulan, for example). In principle, such an enzyme could be used in combination with other amylolytic activities for development of new approaches to complete hydrolysis of starch, provided that a proper combination of thermostable activities could be obtained to produce at least 96% DX.

For example, a thermophilic bacterium known as $Thermoanaerobacter\ finnii$ has been shown to produce thermostable amylase and pullulanase activities which degrade starch completely to maltose (Antranikian, G., 1989, $App.\ Biochem.\ and\ Biotech.,$ 20/21:267–279). These enzymes were produced extracellularly, in the culture medium, a critical advantage for economical production of enzymes on the scale needed for commercial starch hydrolysis. An additional activity needed to complete the conversion of maltose to α-D-glucose, a maltase, was also produced by this organism but only intracellularly. Further, the thermal stability of these enzymes was typified by temperature optima in the range of only 70° C. to 90° C. at pH 5.5, thus affording only marginal performance at the customary temperatures for starch hydrolysis.

An extracellular maltase from the fungus $Paecilomyces\ Varioti$ has been reported (O'Mahony, M. R., et al., 1987, Biotechnology Letters 9:317–322). It has a pH optimum between 3.5 and 4.0, a temperature optimum of 60° C., and a half-life at 60° C. of about 8 hours. Accordingly, this enzyme offers little operational advantage over the intracellular maltase of $T.\ finnii$ described above (Antranikian, G., 1989, supra).

Another frequently reported enzyme activity with potential for starch hydrolysis is that called α-glucosidase. α-glucosidases from various microbial sources exhibit significant diversity in their glucoside substrate specificities. Additionally, these enzymes can be either intracellular, extracellular, or membrane-bound. Thus, classification of these enzymes and functional comparisons between the α-glucosidases from different sources are both difficult problems. Recently, Kelly and Fogerty (1983, Process Biochm. 18:6–12) have proposed a reclassification of bacterial α-glucosidase enzymes into those with highest specific activity toward maltose and those with highest activity toward aryl-D-glucopyranosides.

In principle, an α-glucosidase could be used to help completely digest the products of other starch liquification and saccharification enzymes, to produce high yields of α-D-glucose in novel commercial processes. For example, an α-glucosidase with the proper substrate preference might be used to digest maltose produced by a pullulanase or other enzymes. However, as noted in a recent study (Giblin, M. et al., 1987, Can. J. Microbiol. 33:614–18) typical α-glucosidases from microbial sources are only slightly resistant to heat. In that same report (Giblin, id.), a novel α-glucosidase from the thermophilic bacterium $Bacillus\ caldovelox$ was described. This had a temperature optimum of about 50° C. to 60° C. at pH 5.6 to 6.0 and a half-life of about one hour at 70° C. This enzyme was claimed to be the most thermostable microbial α-glucosidase reported at that time. On the other hand, this enzyme was produced only intracellularly. Further, it showed rather narrow substrate specificity, with its highest specific activity being toward aryl-D-glucopyranosides rather than maltose. Also, this enzyme was unable to attack isomaltose.

Accordingly, there is a continuing need for a variety of microbial starch degrading enzymes which are more thermostable than those presently available, and which can be produced extracellularly to facilitate isolation on the large scale needed for commercial conversion of starch to glucose.

Another process with considerable commercial potential for utilization of thermostable polysaccharide depolymerizing enzymes is the hydrolysis of cellulose, the fibrous matter of all plant tissues. Complete digestion of cellulose to simple sugars requires synergistic action of three types of enzymes: endo-1,4-β-cellulases; exo-1,4-β-glucosidases; and β-D-glucosidases. The latter release D-glucose from soluble cellodextrins and other glycosides including D-cellobiose, a major product of initial cellulose depolymerization steps.

A recent report (Tucker, M. P., et al., 1989, Bio/Technology 7:817–820) on so-called "ultra-thermostable" cellulases from $Acidothermus\ cellulolyticus,$ a thermophilic bacterium from a hot spring in Yellowstone Park, described an extracellular cellulase enzyme complex that produces cellobiose as the final product. An intracellular β-glucosidase from the same source was used for production of the ultimate product, -D-glucose. This latter enzyme dramatically lost activity after reaching 75° C., with the result that practically no activity could be assayed at 90° C. at pH 5.0. In contrast, the two distinct extracellular cellulase activities showed biphasic decay curves upon heating in the absence of substrate, with optima of 75° C. and 83° C. and half-lives of about 12 minutes and less than 3 minutes, respectively, at 90° C. and pH 5.0. A comparative survey of the literature was used to suggest that these cellulases, in particular, possess the highest temperature tolerance reported to date for this class of enzymes. Evidently, the efficiency of commercial hydrolysis of cellulose, for a variety of purposes, is highly constrained by a lack of enzymes with greater thermostability.

Saccharification (i.e., polysaccharide depolymerizing) enzymes from hyperthermophilic bacteria do not appear to be known in the art. Accordingly, a major object of the present invention is to provide methods for producing polysaccharide saccharification enzyme preparations, obtainable from hyperthermophilic bacteria such as *P. furiosus*, produced either extracellularly or intracellularly.

It is also an object of the present invention to provide cell-free and purified polysaccharide depolymerizing enzymes with thermostable activities that are highly desirable for various industrial applications.

SUMMARY OF THE INVENTION

The present invention is based, at least in part, on the finding that hyperthermophilic bacteria, for example, *Pyrococcus furiosus*, can be continuously cultivated at temperatures approaching 100° C. (e.g., 97–99° C.), to provide highly desirable enzymes at a useful rate. Further, it is based on the recognition of the highly unusual, if not unique, metabolic demands placed upon any organism which inhabits an environment that is nearly bereft of other living things and, hence, has little organic matter from which to obtain complex nutrients.

Thus, the present inventors have considered the possibility that *Pyrococcus furiosus* and other organisms sharing similar environments may have acquired efficient capabilities to digest whatever complex substrates, such as polysaccharides, for instance, that may be available and are otherwise relatively stable in the ocean depths at high temperature. These ambient polysaccharides might be expected to include, for example, cellulose and starch from plant vegetation and, perhaps, chitin from crustaceans.

Accordingly, the present inventors have found that *P. furiosus* produces several starch hydrolyzing enzymes, both extracellularly and intracellularly, which retain their activity for several hours at or above 100° C. These comprise an α-glucosidase, which has been highly purified, and amylolytic enzymes including an amylase and a pullulanase. In addition, at least one thermostable enzyme activity from *P. furiosus* that is useful in the process of degradation of cellulose to D-glucose has also been found, namely a β-glucosidase, which is also active up to at least 95° C. Furthermore, addition of appropriate carbohydrate substrates to cultures of *P. furiosus* has been found to induce enhancement of both extracellular and intracellular production of saccharification enzymes, usually those activities involved in degradative metabolism of the particular added substrate. The present invention thus enables production of such extremely thermostable saccharification enzymes for industrial applications, either directly from hyperthermophilic bacteria such as *Pyrococcus furiosus*, or from other more easily cultivated microorganisms through the use of genetic engineering technology that is now well known in the art.

Thus, in one aspect the present invention relates to a cell-free enzyme preparation obtainable from a hyperthermophilic bacterium, for example, *Pyrococcus furiosus*, having activities of the following enzymes: an amylase, a pullulanase, an α-glucosidase and a β-glucosidase. Each of these activities is distinguishable by its substrate specificity and thermal stability. This preparation is obtainable from *P. furiosus* by a process comprising the steps of cultivating cells of the bacterium in nutrient medium, collecting the cells from the medium, disrupting the cells, and removing the resulting insoluble cell debris, which results in a cell-free extract that contains these enzymes.

Culture medium of *Pyrococcus furiosus* also contains a variety of saccharification enzyme activities, the levels of which vary according to the composition of the nutrient medium. Their presence in the medium evidently results from extracellular enzyme production. Accordingly, the enzyme preparation of the present invention is also obtainable from *Pyrococcus furiosus* by a process comprising the steps of cultivating cells of the bacterium in nutrient medium and removing the cells from the medium, which results in cell-free medium that contains these enzymes.

The products resulting from the action of the enzyme preparation of this invention on various saccharide, as determined by thin-layer chromatography, indicate that this preparation is able to produce monomeric and oligomeric saccharides from starch, pullulan and glycogen. The preparation is able to convert a substantial portion of the starch completely to monomer after 72 hours at 85° C. Although some oligomeric intermediates remain under the limited range of test conditions that have been tried, the apparent lack of accumulation of any particular intermediate indicates that, under proper conditions, the enzymes in the preparation of this invention can completely digest starch to glucose (i.e., achieve at least 96% DX). The major product from digestion of pullulan is a trimer (maltotriose). Only a minor amount of monomeric product is visible in dextran samples exposed to this enzyme preparation According to a principal embodiment of this aspect of the present invention, the strain of *Pyrococcus furiosus* used for the cell-free enzyme preparation is derived from the deposit DSM 3638 of the Deutsche Sammlung von Mikroorganismen, Federal Republic of Germany.

In the enzyme preparation according to this invention, the activities of the amylase, pullulanase, and α-glucosidase upon assay at pH 5.6 increase with increasing temperature in the range of 50° C. to at least about 108° C. Due to technical limitations of currently available methods for enzyme assays at temperatures substantially above the boiling point of water, that actual temperature optima for these enzyme activities have not been determined.

For comparison, as indicated in the Background, it is believed that the most extreme thermostability previously reported for a pullulanase activity, as well as for a maltase activity, was typified by temperature optima in the range of only 70° C. to 90° C. at pH 5.5 (Antranikian, G., 1989, *App. Biochem. and Biotech.*, 20/21:267–279; O'Mahony, M. R., et al., 1987, Biotechnology Letters 9:317–322). For an α-glucosidase, the most thermostable enzyme reported had a temperature optimum of about 50° C. to 60° C. at pH 5.6 to 6.0 and a half-life of about one hour at 70° C. (Giblin, M. et al., 1987, Can. J. Microbiol. 33:614–18).

Further, in this enzyme preparation of the present invention, the half-life of the activity of the amylase at pH 5.6 and 98° C., in the absence of substrate, with no added stabilizing agent, is about 4 hours; the half-life of the activity of the pullulanase at pH 5.6 and 98° C., in the absence of substrate, with no added stabilizing agent, is about 7 hours; and the half-life of the activity of the α-glucosidase at pH 5.6 and 98° C., in the absence of substrate, with no added stabilizing agent, is about 8 hours.

It is known that cell-free enzyme preparations of the present invention contain thermostable proteolytic enzyme activities which are highly active at 98° C. (see U.S. patent application Ser. No. 07/406,327, filed Sep. 12, 1989). Therefore, these activities may substantially reduce the half-lives of the present enzyme activities compared to the stabilities of the same enzymes that would be observed in the absence of this protease. (See, for example, the approximately 5 fold increase in thermostability of the α-glucosidase upon purification, Example 3, below.)

Another aspect of the present invention relates to a purified α-glucosidase obtainable from *Pyrococcus furiosus* and having activities on the following substrates at 95° C. and pH 5.6, in descending order, as follows: isomaltose, maltose, methyl-α-D-glucopyranoside, and p-nitrophenol-α-D-glucopyranoside. This purified α-glucosidase has a pH optimum between about pH 5.2 and pH 5.8 at 98° C., and shows no significant loss of activity during assay at pH 5.6 over the temperature range of 105° C. to 115° C., the highest temperature that has been tested so far due to technical limitations of enzyme assays at elevated temperatures. The half-life of the activity of the purified α-glucosidase at pH 5.6 and 98° C., in the absence of substrate, with no added stabilizing agent, is about 40 hours. The α-glucosidase of this invention has been purified at least 310-fold and comprises a single polypeptide having an approximate molecular mass value of about 125 kilodaltons (kDa) as determined by electrophoresis in polyacrylamide gels in the presence of SDS. Purification and characterization of this α-glucosidase is described in detail in Example 3, below.

In yet another aspect, the present invention also relates to a cell-free preparation of β-glucosidase from *Pyrococcus furiosus* having activity at 95° C. and pH 5.6 that is greater on p-nitrophenol-β-D-glucopyranoside than its activity on p-nitrophenol-α-D-glucopyranoside. The majority of this β-glucosidase is not bound to an anion exchange resin in the absence of salt under slightly basic pH conditions (e.g., at pH 8.5), as described in Example 3, below, indicating that at least one major component of this activity is vested in an acidic protein. Further, the β-glucosidase activity resides in at least two molecularly distinct species, one of which has a relative mobility about 2.4 times higher than that of the α-glucosidase of the present invention, upon electrophoresis under nondenaturing conditions, and the other of which has a relative mobility about 7.0 times lower than that of this same α-glucosidase under the same conditions.

This invention also relates to a process for producing a cell-free enzyme preparation from *Pyrococcus furiosus* having activities of the following enzymes: an amylase, a pullulanase, an α-glucosidase and a β-glucosidase, comprising the steps of: cultivating cells of the bacterium in nutrient medium at a temperature of about 98° C. under an anaerobic atmosphere at ambient pressure, under conditions of continuous steady-state culture, and where the nutrient medium comprises sea water containing complex carbon sources, and optionally, elemental sulfur; and separating said cells from said medium, which results in cell-free medium that contains the enzymes. Further, optionally, the enzymes inside the cells are prepared by the additional steps of disrupting the cells and removing the resulting insoluble cell debris, which results in a cell-free extract that contains said enzymes.

This process of for obtaining cell-free preparations of saccharification enzymes from a hyperthermophilic bacterium, such as *Pyrococcus furiosus*, for instance, is advantageously coupled with a method for continuous steady-state culture of such organisms which has been developed by the present inventors (Example 1). The yields per unit of culture medium and the reductions in labor and downtime for equipment cleaning of this approach compare quite favorably to the more usual batch approaches for cultivation of bacteria which grow only at lower temperatures.

An embodiment of this overall enzyme production method which incorporates this simple continuous culture method is described herein for producing saccharification enzymes, in which advantageously the cultivating of the *Pyrococcus furiosus* is at a temperature of about 98° C. under an anaerobic atmosphere at ambient pressure, under conditions of continuous steady-state culture, and where the nutrient medium comprises sea water containing complex carbon sources, and optionally, for better growth, elemental sulfur.

The present inventors have also discovered that addition of various oligosaccharides or polysaccharides to a culture of *P. furiosus* enhances production of saccharification enzymes. Therefore, the present invention also relates to the process for producing a cell-free enzyme preparation described above where the nutrient medium further comprises an amount of carbohydrate substrate effective for enhancing production of any of the enzyme activities described above. Evidently, substrates with (1,4) glucose linkages enhance production of all the saccharification enzymes in the preparation of this invention, including the β-glucosidase, although different substrates have differential effects on the different enzymes and their relative distributions inside the cells or in the medium. Advantageously for enhancement of total enzyme production, this substrate is maltose, pullulan, starch or glycogen.

In a most preferred embodiment of this process, the nutrient medium further comprises an amount of polysaccharide substrate effective for enhancing production of any of the enzymes in the culture medium. Most advantageously, this substrate is starch or glycogen.

Thus, compared to using complex carbon sources (yeast extract and tryptone) with elemental sulfur, addition of maltose, starch or glycogen enhances production of the total level of each of the three saccharification enzyme activities, amylase, pullulanase, and α-glucosidase, in either the cells or the culture medium or both, by factors ranging from about 3 to 50 fold. The best yields per liter of culture of each enzyme obtained so far, with substrate added to the culture as indicated, are as follows: amylase (glycogen, enzyme in medium) 60,100 units; pullulanase (maltose, intracellular) 8020 units; and α-glucosidase (glycogen, intracellular) 9584; β-glucosidase (starch, intracellular) 220 units.

The present invention may be understood more readily by reference to the following detailed description of specific embodiments and the Figures and Examples included therein.

DESCRIPTION OF SPECIFIC EMBODIMENTS

The present invention relates to a cell-free enzyme preparation obtainable from the hyperthermophilic bacterium *Pyrococcus furiosus*, having activities of the following enzymes: an amylase, a pullulanase, an α-glucosidase and a β-glucosidase. Each of these activities is distinguishable by its substrate specificity and thermal stability. Thus, the amylase was detected by its ability to degrade soluble starch as measured in a standard amylase assay, by the amount of reducing sugar released. Similarly, for pullulanase, pullulan was used as substrate and activity was measured by the amount of reducing sugar released. For these enzymes, one unit of enzyme activity was defined as the amount of enzyme that released one nmol of reducing sugar (as a glucose standard) per minute under the assay conditions used (see Example 2). α-Glucosidase was assayed using p-nitrophenyl-β-D-glucopyranoside (PNP-α-G) as substrate, and β-glucosidase was assayed using p-nitrophenyl-β-D-glucopyranoside (PNP-β-G) as substrate. One unit of glucosidase activity was that amount of enzyme releasing one μmol PNP per minute under the standard conditions, from the appropriate α or β substrate.

In a preferred embodiment of this aspect of this invention, the *Pyrococcus furiosus* is the strain of deposit DSM 3638 of the Deutsche Sammlung von Mikroorganismen, Federal Republic of Germany. This deposit is accessible to the public without restriction. Accordingly, access to the deposit by the Commissioner during pendency of this application, "reasonable" permanent availability of the culture, and access to the culture by the public upon issuance of the patent are all assured by means of this deposit.

The present invention is based, at least in part, on the finding that hyperthermophilic bacteria, for example, *Pyrococcus furiosus*, can be continuously cultivated at temperatures approaching 100° C. (e.g., 97–99° C.), to provide desirable enzymes at a useful rate. The general growth characteristics of *P. furiosus*, a heterotrophic anaerobe isolated by Stetter and Fiala (Fiala, G. and Stetter, K. O., 1986, Arch. Microbiol. 145:56–61) from shallow thermal waters near Vulcano Island, Italy, have been described previously (Brown, S. H. & Kelly, R. M., 1989, *Appl. Environ. Microbiol.* 55:2086–2088). Specific details of cultivation media and methods developed for production of enzymes from *P. furiosus* cells, either in batch cultures or under continuous, steady-state conditions, are described in Example 1, below.

According to this aspect of the present invention, a cell-free preparation of saccharification enzymes is exemplified by a soluble *P. furiosus* cell extract that is obtainable from this bacterium by a process comprising the steps of cultivating cells of this bacterium in nutrient medium, collecting the cells from the medium by centrifugation, disrupting the cells by sonication, and removing the resulting insoluble cell debris by high speed centrifugation, as described in further detail in Example 2. This process results in a cell-free extract which constitutes the enzyme preparation.

Figure 1:
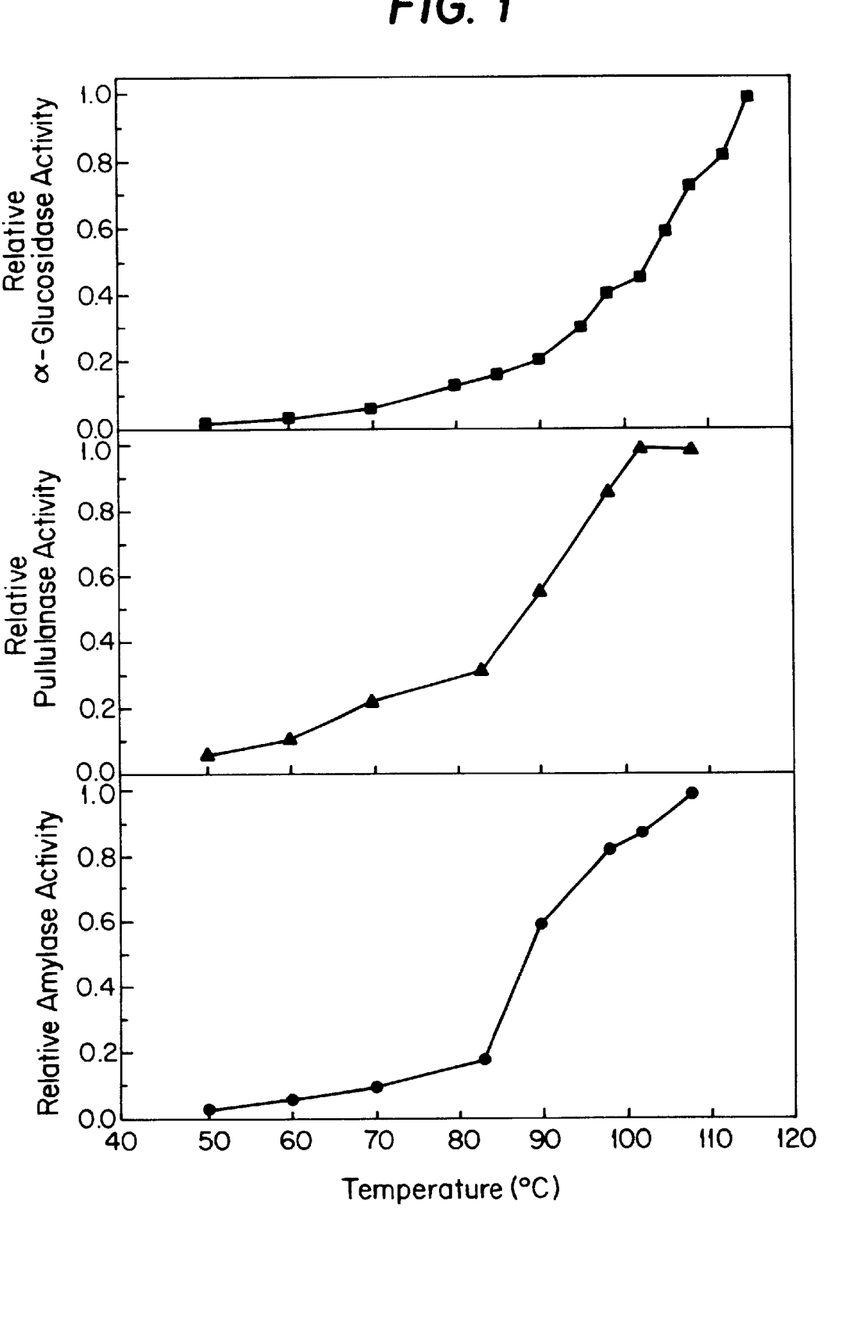
FIG. 1. Relative levels of saccharification enzyme activities in cell-free preparation of *Pyrococcus furiosus* as a function of assay temperature. Samples of cell-free extract preparation were incubated at the indicated temperatures for 30 min. under standard assay conditions using appropriate substrates for each activity. Top panel: α-glucosidase activity. Middle panel: pullulanase activity. Bottom panel: amylase activity.

The saccharification enzyme activities in the cell-free extract from *P. furiosus* increased from 37° C. to at least about 108° C., as shown in FIG. 1. Some activities appeared to be still increasing at 108° C.; however, the temperature optima for the activities of this extract cannot be determined using the standard assays described here, due to a lack of suitable equipment for measuring the necessary optical densities above this temperature. In particular, commercially available cuvettes for the necessary spectrophotometric readings are not able to be sealed above about 108° C. Accordingly, the temperature optima are not yet known for the several saccharification activities within this extract or for its individual components.

Figure 2:
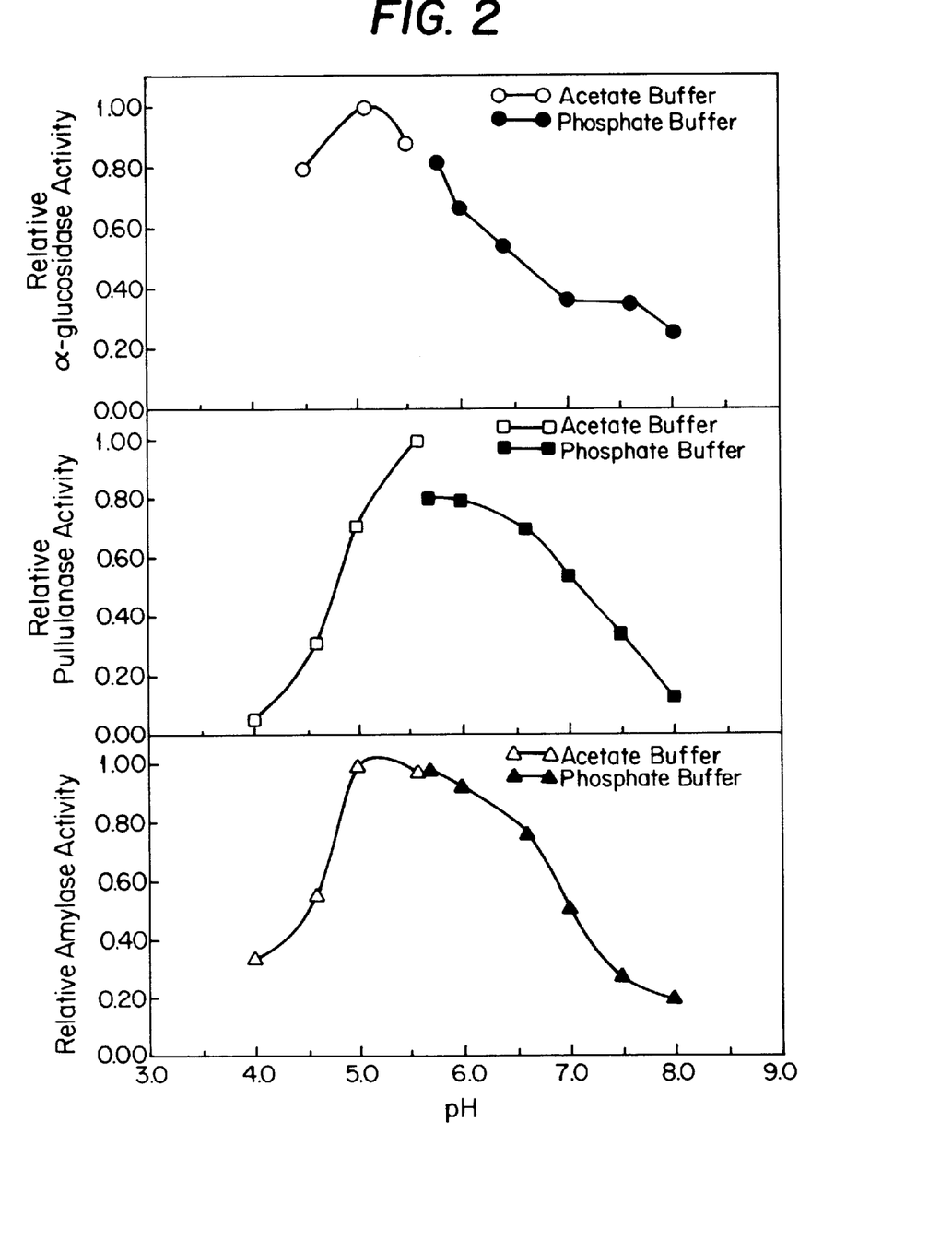
FIG. 2. Effect of pH on saccharification enzyme activities at 98° C. of a cell-free enzyme preparation from *Pyrococcus furiosus*. Samples of cell-free extract preparation were incubated at the indicated temperatures for 30 min. under standard assay conditions using appropriate substrates for each activity. For pH values of 4.0 to 5.6, 0.1 M sodium acetate-acetic acid buffer was used, while from pH 5.7 to 8.0, 0.1 M sodium phosphate buffer was used. Top panel: α-glucosidase activity. Middle panel: pullulanase activity. Bottom panel: amylase activity.

The effects of pH on the levels of saccharification enzyme activities in the cell-free preparation of this invention have been determined over the range of pH 4.0 to pH 8.0. The results (FIG. 2) indicate that the activities of the amylase, pullulanase, and the α-glucosidase all are active over a broad range of pH values, with optima in the range of pH 5.0 to pH 6.0. Thus these activities are well-suited to operation at the acid pH conditions employed in current starch hydrolysis operations.

Figure 3:
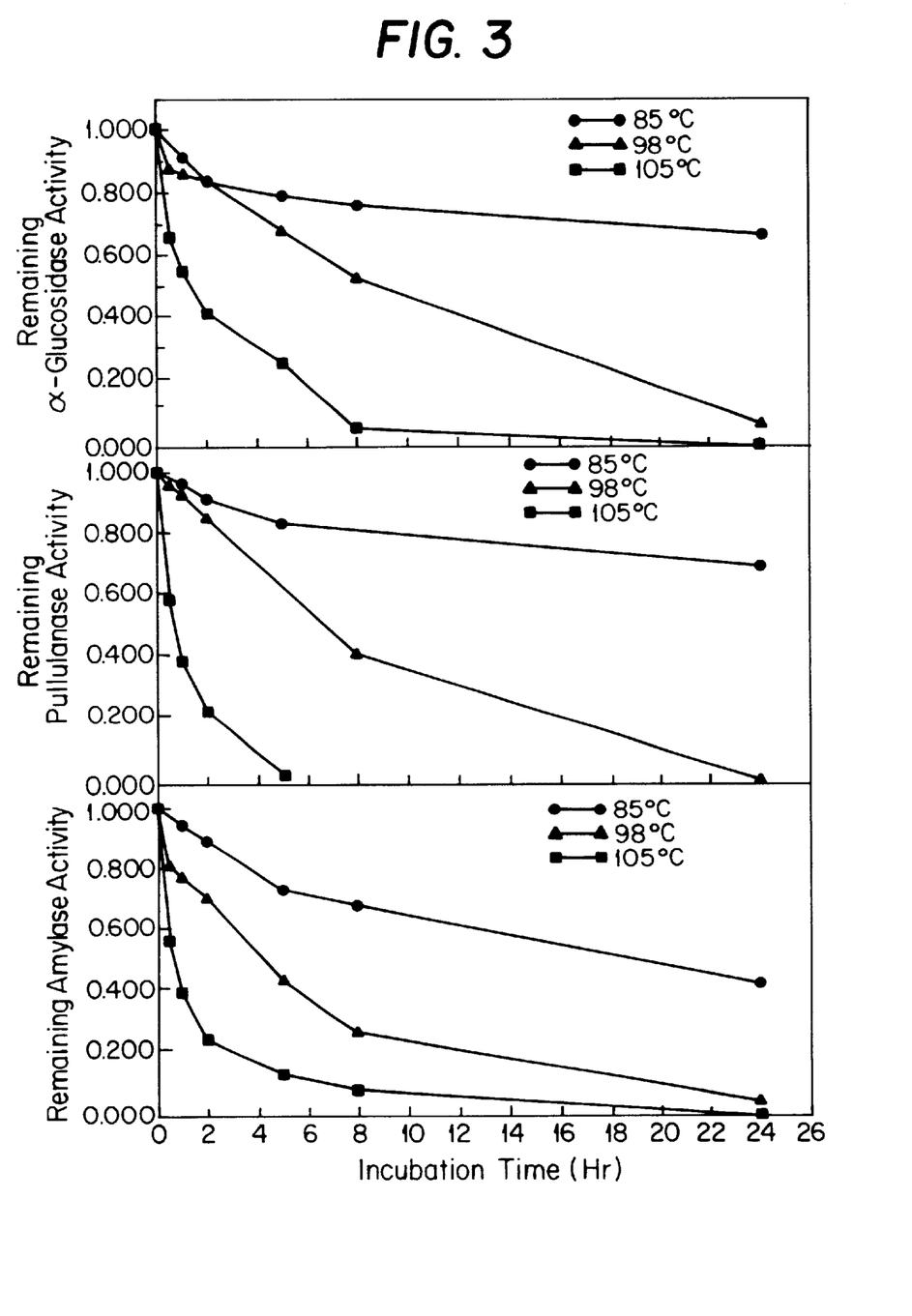
FIG. 3. Thermostability of saccharification enzyme activities (assayed at 98° C.) in a cell-free preparation of *Pyrococcus furiosus* as a function of time of incubation prior to assay, without substrate, at pH 5.6, at 85° C., 98° C. or 105° C., as indicated by the symbols defined in the figure. Top panel: α-glucosidase activity. Middle panel: pullulanase activity. Bottom panel: amylase activity.

The half-life of several enzymatic activities of the cell-free extract of the present invention were determined at pH 5.6, under various conditions relevant to current industrial processes for starch hydrolysis (see FIG. 3, bottom panel). At 85° C. in the absence of substrate, with no added calcium, amylase activity of the cell-free *P. furiosus* enzyme preparation shows a half-life of about 20 hours (see FIG. 3, bottom panel). Under the same conditions, at 95° C., the amylase shows a biphasic decay with 20% loss of activity in under one hour; but then 50% of the total activity remains at 4 hours (FIG. 3). At 105° C., the half-life for amylase was reduced to about 20 minutes.

Low levels of calcium ion (e.g., 5 mM) improve the thermostability at pH 5.6 of the amylase activity of the present invention, but only slightly. Thus, if calcium ion is essential for stabilizing this activity, sufficient calcium for this purpose must remain bound to the protein, even after dialysis as in the method of preparation used in Example 2.

For the pullulanase, at pH 5.6 and 98° C. in the absence of substrate, with no added calcium, activity of the cell-free *P. furiosus* enzyme preparation shows an estimated half-life of at least about 7 hours. Under the same conditions at 105° C., the half-life for pullulanase was reduced to about one hour (FIG. 3, middle panel). Calcium appears to stabilize this activity more than the amylase activity, as indicated, for example, by increasing the amount of activity after incubation at 85° C. under the above conditions for about 10.5 hours, from about 70% without added calcium, to over 95% with calcium added (5 mM).

For the α-glucosidase, at pH 5.6 and 98° C. in the absence of substrate, with no added calcium, activity of the cell-free *P. furiosus* enzyme preparation shows an estimated half-life of at least about 8 hours. Under the same conditions at 105° C., the half-life for α-glucosidase activity was reduced to slightly over one hour (FIG. 3, top panel). Added calcium appears to exert relatively little stabilizing effect on this activity.

Saccharification enzyme activities were also detected in culture medium of *P. furiosus* after removal of cells by centrifugation and concentration of the cell-free medium by cross-current filtration. These preparations contain activities that were not distinguished in substrate specificity or stability from those produced in soluble extracts of cells, indicating that the cell-free culture medium is also a useful source of thermostable saccharification enzymes of the present invention.

The products resulting from the action of the enzyme preparation of this invention on various saccharide, as determined by thin-layer chromatography, indicate that this preparation is able to produce monomeric and oligomeric saccharides from starch, pullulan and glycogen. More specifically, the products resulting from the action of the enzyme mixture on various saccharide substrates were examined using thin-layer chromatography. Two sets of samples were run. For the first set, 200 l each of a dialyzed cell extract (pH 5.6) from a *P. furiosus* culture grown on 5 g/l starch. All substrates were prepared in 0.1M sodium acetate buffer, pH 5.6. These samples were held at 98° C. for 0.5 hour and quenched on ice.

The second set of samples were used to examine the results from an extended hydrolysis of starch. 1.0 ml of the enzyme mixture described above was added to 2% starch in 0.1M acetate buffer (pH 5.6) and held at 85° C. for several days. Samples were withdrawn from this reaction mixture at various times and quenched on ice. This experiment was repeated using a concentrated supernatant sample from *P. furiosus* grown on 5 g/l starch.

Thin-layer chromatography as described by Hansen was used to examine the products resulting from the above reactions. 3×1 μl samples were applied to aluminum sheet silica gel 60 TLC plates (Merck #5553) which had been pre-conditioned at 105° C. for 1 hour prior to use. Samples were allowed to dry at room temperature, and the plates were placed upright in a developing tank containing a solvent system consisting of propan-2-ol-acetone-1M lactic acid (2:2:1). After approximately 3 hours, the plate was removed from the tank and dried with an air stream. Sugar spots were developed by spraying the plates with aniline-diphenylamine-acidified acetone reagent (Sigma #A8142) and holding them for 1 hour at 105° C. A solution of saccharide standards was also applied to each plate, and contained 0.1% of the following sugars in DI $H_2O$: glucose ($DP_1$), maltose ($DP_2$), maltotriose ($DP_3$), maltotetraose ($DP_7$).

Figure 4:
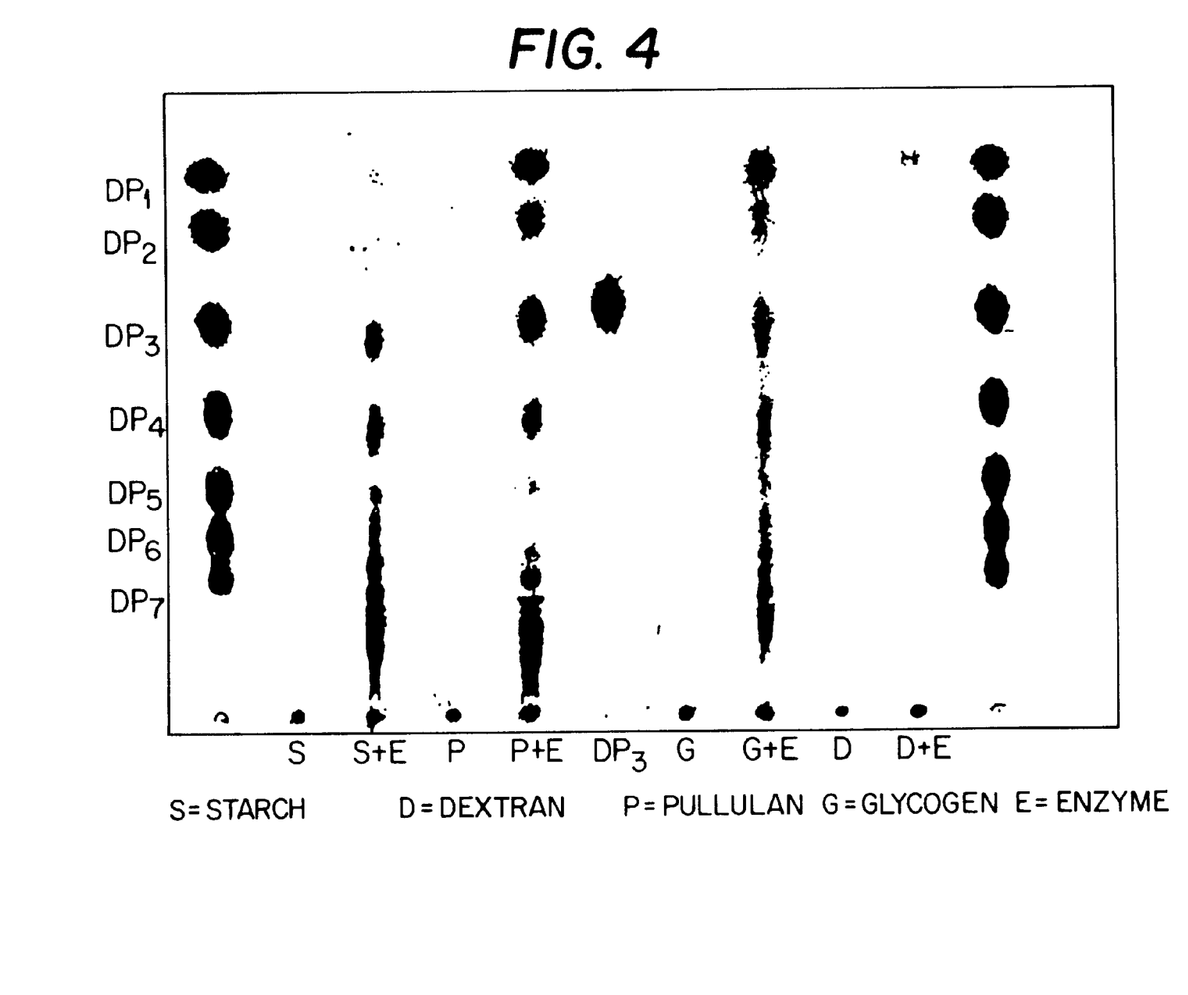
FIG. 4. Analyses of digestion products by thin layer chromatography (after short-term hydrolysis) produced by the cell-free enzyme preparation showing that it is able to produce saccharides of monomeric ($DP_1$) and oligomeric forms ($DP_2$, etc.,) from starch (S), pullulan (P) and glycogen (G), while hydrolysis of dextran (D) is minimal. Samples with and without enzymes (E) were run side by side.

Results from the first experiment (see FIG. 4 (short-time hydrolysis) indicate that the crude enzyme mixture is able to produce saccharides of $DP_1$ and higher from starch, pullulan and glycogen. The major product from pullulan is $DP_3$, and only a trace of $DP_6$ is visible. A minor amount of $DP_1$ is visible in the dextran sample, and this is most likely the result of abiotic hydrolysis.

Figure 5:
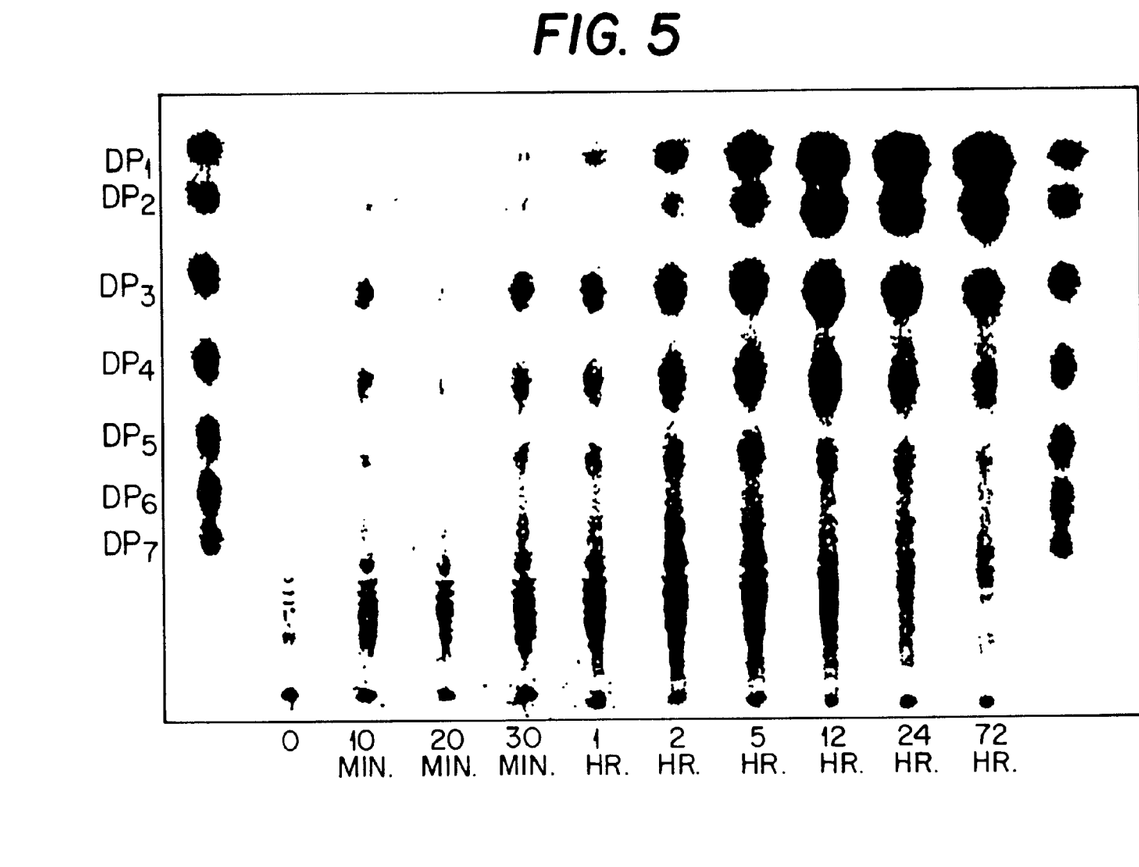
FIG. 5. Analyses of kinetics of digestion of starch by thin layer chromatography (after short-term hyrdrolysis) produced by the cell-free enzyme preparation showing that it is able to convert a substantial portion of the starch completely to monomer ($DP_1$) after 72 hours at 85 C., although some oligomers ($DP_2$ through $DP_4$) are still present under these conditions.
Figure 6:
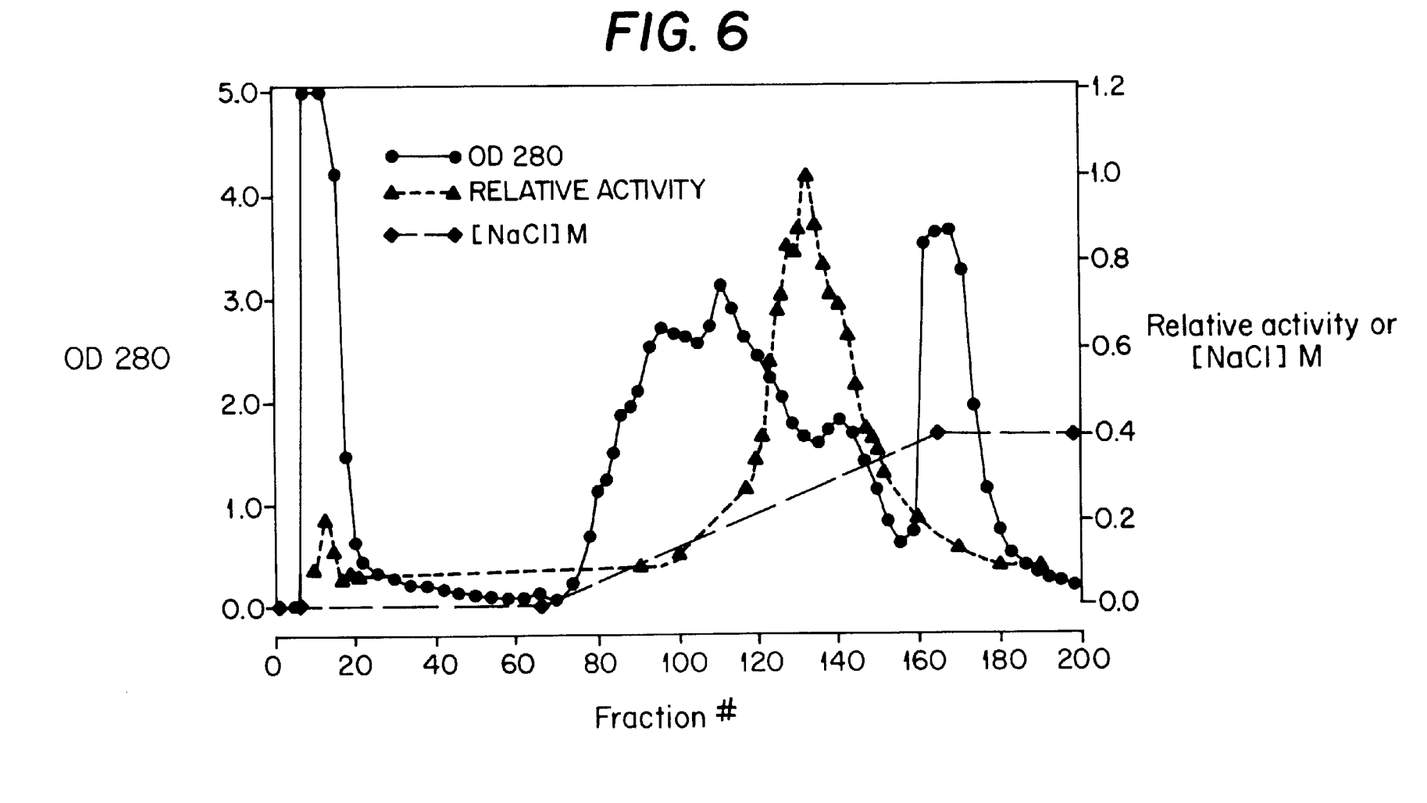
FIG. 6. Anion exchange chromatography of *Pyrococcus furiosus* α-glucosidase on DEAE-cellulose. Protein mass (OD 280), α-glucosidase activity and NaCl concentration are indicated in the figure.
Figure 7:
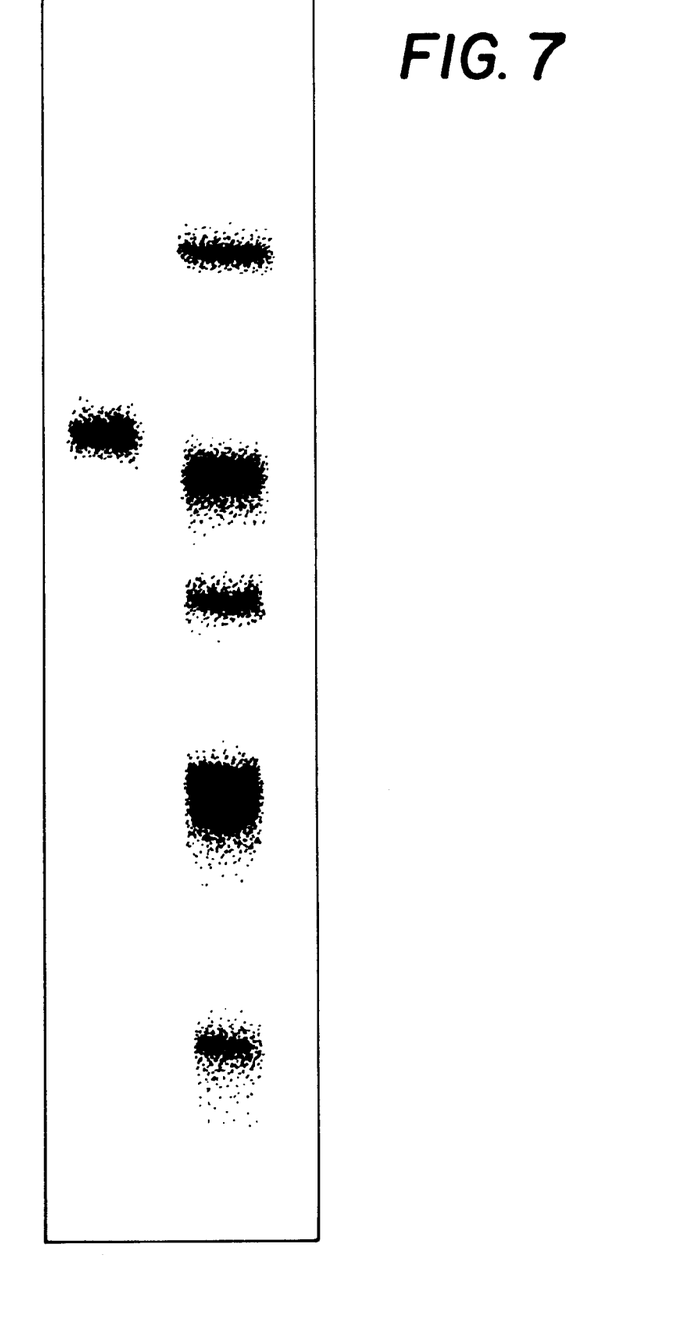
FIG. 7. Electrophoresis of purified *Pyrococcus furiosus* α-glucosidase in acrylamide gels with detergent (SDS). Purified enzyme (0.5 μg) was run in the left lane. The right lane contains protein molecular weight standards (top to bottom): myosin (206 kDa), β-galactosidase (116.25 kDa), phosphorylase B (97.4 kDa), bovine serum albumen (66.2 kDa), and ovalbumin (42.7 kDa).

Results from the time course experiment (see FIG. 5) indicate that the crude enzyme mixture is able to convert a substantial portion of the starch completely to $DP_1$ after 72 hours at 85° C., although some $DP_2$ through $DP_4$ are still present. The shift to products of lower DP as the reaction progresses is readily apparent.

Figure 8:
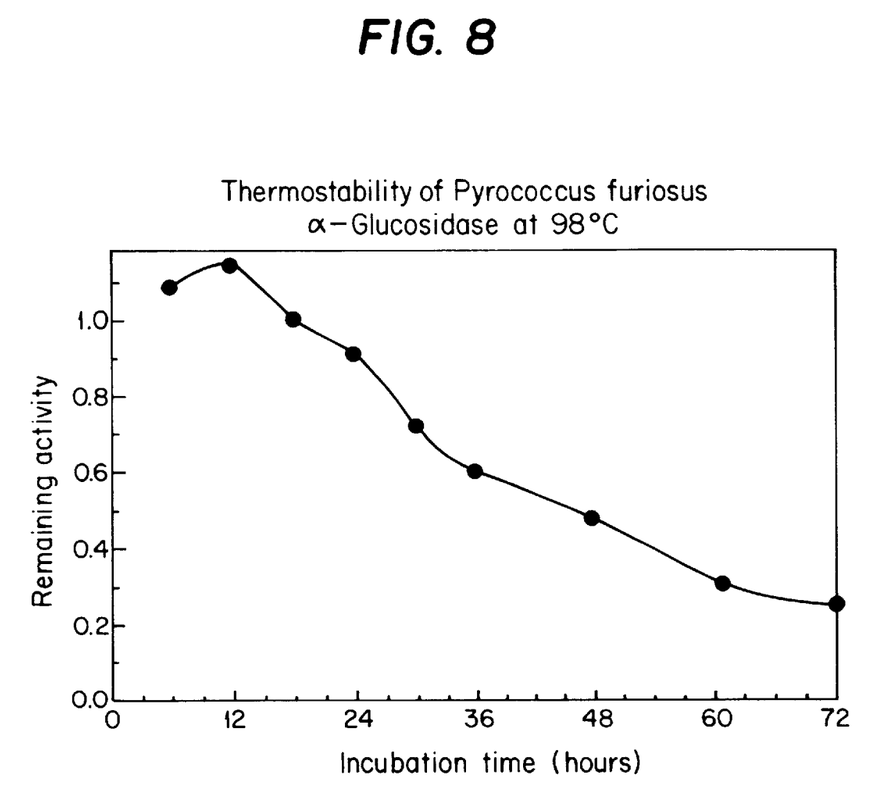
FIG. 8. Thermostability of the purified α-glucosidase of *Pyrococcus furiosus* (assayed at 98° C.) as a function of time of incubation prior to assay, without substrate, at pH 5.6. Purified enzyme was incubated 98° C. for various times, as indicated in the figure.

This purified α-glucosidase has a pH optimum between about pH 5.2 and pH 5.8 at 98° C., and shows no significant loss of activity during assay at pH 5.6 over the temperature range of 105° C. to 115° C., the highest temperature that has been tested so far due to technical limitations of enzyme assays at elevated temperatures (see FIG. 8). The half-life of the activity of the purified α-glucosidase at pH 5.6 and 98° C., in the absence of substrate, with no added stabilizing agent, is about 40 hours. Further, this purified α-glucosidase preparation of the present invention has resistance to inactivation by either 1% sodium dodecyl sulphate or 1 molar urea that is characterized by 22% and 84% retention of activity at 98° C. for at least 30 minutes.

In yet another aspect, the present invention also relates to a cell-free preparation of β-glucosidase from *Pyrococcus furiosus* having activity at 95° C. and pH 5.6 that is greater on p-nitrophenol-β-D-glucopyranoside than its activity on p-nitrophenol-α-D-glucopyranoside, under assay conditions described in Example 2.

Further, the β-glucosidase activity resides in at least two molecularly distinct species, as revealed by electrophoresis in polyacrylamide gels under nondenaturing conditions (see Example 3). A preparation of cell-free extract from *P. furiosus* was prepared as in Example 2, and aliquots were loaded on several lanes of a single gel. Different lanes of the gel were then separately assayed for α-glucosidase or β-glucosidase activity (see Example 3). The results showed essentially a single intense band of α-glucosidase activity in one lane and several bands of β-glucosidase in an adjacent lane. A faint band of β-glucosidase activity appeared exactly in the same position as the single α-glucosidase band. In addition, bands of β-glucosidase activity with intensity about equal to the α-glucosidase band were also observed. One of these species has a relative mobility about 2.4 times higher than that of the α-glucosidase of the present invention, during electrophoresis under denaturing conditions, and the other of which has a relative mobility about 7.0 times lower than that of this same α-glucosidase under the same conditions. An additional faint band of β-glucosidase activity was observed with a relative mobility about 1.6 times higher than that of the α-glucosidase of the present invention.

This invention also relates to a process for producing a cell-free enzyme preparation from *Pyrococcus furiosus*, having activities of the following enzymes: an amylase, a pullulanase, an α-glucosidase and a β-glucosidase, comprising the steps of: cultivating cells of the bacterium in nutrient medium and separating the cells from the medium. This process is then continued for either preparing intracellular enzymes, by the additional steps of disrupting the cells and removing the resulting insoluble cell debris, resulting in said cell-free enzyme preparation; or, in the alternative, for utilizing extracellular enzymes in sa id medium, by the additional optional steps of concentrating and isolating said extracellular enzymes.

The levels of activity of the several saccharification enzymes from *Pyrococcus furiosus*, obtainable from either the cells or the medium, with addition of various carbohydrate substrates, are summarized in Table 1, below:

TABLE 1

Effect of adding substrate to the culture medium on saccharification enzyme production by *P. furiosus*.

| Sample | | Amylase | | Pullulanase Sp. | | β-Glucosidase | |
|---|---|---|---|---|---|---|---|
| Medium | Fraction | Sp. Act. (U/mg) | Tot. Act. (U) | Act. (U/mg) | Tot. Act. (U) | Sp. Act. (U/mg) | Tot. Act. (U) |
| Complex | pellet | 41 | 350 | 48 | 405 | 140 | 1170 |
| C/S° | supernate | 138 | 1380 | 38 | 380 | 29 | 292 |
| Maltose/ | pellet | 285 | 6460 | 361 | 8020 | 254 | 5640 |
| S° | supernate | 682 | 5000 | 503 | 3690 | 39 | 289 |
| Starch/ | pellet | 190 | 6280 | 138 | 4540 | 280 | 9200 |
| S° | supernate | 1740 | 20,190 | 302 | 3490 | 57 | 653 |
| Glycogen/ | pellet | 196 | 2718 | 320 | 4440 | 691 | 9584 |
| S° | supernate | 1975 | 60,100 | 98 | 2980 | 80 | 2435 |
| Dextran/ | pellet | 116 | 970 | 103 | 861 | 262 | 1889 |
| S° | supernate | 62 | 2876 | 19 | 881 | 5 | 220 |

EXAMPLE 1

Continuous Cultivation of *Pyrococcus furiosus* for Enzyme Production

A system has been developed which allows continuous cultivation of hyperthermophilic archaebacteria at temperatures approaching 100° C. Using this system, continuous cultivation of the hyperthermophile, *Pyrococcus furiosus*, was carried out and the resulting dilution rate and gas production profiles were determined. These results have been published (Brown, S. H. & Kelly, R. M., 1989, Appl. Environ. Microbiol. 55:2086–2088, the entirety of which is hereby in incorporated herein by reference).

In this example are parameters for the design and operation of a system which allows continuous cultivation of hyperthermophilic bacteria at temperatures approaching 100° C. These parameters have been presented in U.S. patent application Ser. No. 07/406,327, filed Sep. 12, 1989, the entirety of which is hereby incorporated herein by reference.

*Pyrococcus furiosus* is a hyperthermophilic archaebacterium which grows optimally at 98–100° C. This organism was first isolated from shallow geothermal marine sediments by Fiala and Stetter (supra). It is an obligatedly anaerobic heterotroph, and grows in both the presence or absence of elemental sulfur. When sulfur is present, $H_2S$ and $CO_2$ are produced as a consequence of growth, along with trace amounts of $H_2$. In the absence of sulfur, only $CO_2$ are produced, and the $H_2$ eventually becomes inhibitory to cell growth. The relationship between the production of these gases, particularly $H_2S$, and the metabolism of *P. furiosus* has not yet been determined. *P. furiosus* can reach cell densities of over $10^8$ cells/ml, which is relatively high for this class of organisms, making it an attractive candidate for production of enzymes for industrial applications according to the present invention.

*Pyrococcus furiosus* (DSM 3638) was grown in artificial sea water supplemented with 0.1% yeast extract and 0.5% tryptone (Difco Laboratories, Detroit, Mich.). The artificial sea water was modified from Kester et al. (Kester, D. R., et al., 1967, Limnol. Oceanogr. 12:176–178) and was formulated as follows: Solution A, 47.8 g/l NaCl, 8.0 g/l $Na_2SO_4$, 1.4 g/l KCl , 0.4 g/l $NaHCO_3$, 0.2 g/l KBr, and 0.06 g/l $H_3BO_3$; Solution B, 21.6 g/l $MgCl_2.6H_2O$, 3.0 g/l $CaCl_2.2H_2O$, 0.05 g/l $SrCl_2.6H_2O$; Solution C, 12.5 g/l $NH_4Cl$, 7.0 g/l $K_2HPO_4$, and 50.0 g/l $CH_3CO_2Na$. Equal volumes of solutions A and B were mixed while stirring, the yeast extract and tryptone were added, and the resultant solution was sterilized by autoclaving. Solution C was sterilized separately, and 20 ml was added aseptically to 980 ml of the above mixture after cooling. Anaerobic conditions were achieved by flushing the medium with prepurified $N_2$ (Linde Gases, Baltimore, Md.) and adding 0.5 g/l $Na_2S$ (after autoclaving). Resazuring (1.0 mg/l) was used as a redox indicator. The final pH of the medium after sulfide addition was approximately 6.8

For continuous culture, the culture vessel was a 5-neck round bottom flask (Lab. Glass Inc., Vineland, N.J.) with a total volume of 2 liters. A gas inlet tube was used to sparge the vessel, and the gas stream exiting the reactor was passed through a Graham condenser to reduce water losses, and then through a gas washing bottle containing 3.0 N NaOH to remove $H_2S$. Samples for gas analysis were taken through a rubber septum mounted on the condenser outlet. The temperature in the culture vessel was maintained at 98 C. using a heating mantle, proportional temperature controller, and a type J thermocouple (Cole-Parmer Instrument Co., Chicago Ill.) Although *P. furiosus* grows optimally at 100 C., operation slightly below this optimum prevents a boiling, while supporting growth rates close to the maximum.

Medium for continuous culture experiments was added aseptically to sterile polycarbonate or polypropylene carboys (Nalge Co., Rochester, N.Y.) and maintaining under anaerobic conditions by purging with prepurified $N_2$ that was filtered through a 0.2 μm filter (Gelman Sciences, Ann Arbor, Mich.). This culture medium was added to the reactor using a Masterflex peristaltic pump (Cole-Parmer) with a size 14 pump head. A constant reactor volume was maintained using a dip tube and a size 16 pump head connected in parallel with the inlet pump. Teflon PFA tubing (Cole-Parmer) was used between the feed reservoir and the reactor, except for a short section of silicone tubing in the pump head itself. Inlet tubing was autoclaved and aseptically connected to the medium reservoir and the reactor using Luer Lock fittings (Popper & Sons, New Hyde Park, N.Y.). A miniature double-junction pH electrode (phoenix Electrodes, Houston, Tex.) and a Chemcadet pH controller (Cole-Parmer) were used to monitor pH in the reactor. Teflon thermometer adapters with Viton O-rings (Cole-Parmer) were used to hold the thermocouple, inlet and outlet tubes, and pH probe in the 24/40 joints of the culture flask.

Reactor inocula were grown in sealed 125 ml serum bottles containing 50 ml of the above medium along with 10 g/l elemental sulfur. These bottles were maintained under quiescent conditions at 98 C. in a temperature bath (New Brunswick Scientific Co., Inc., New Brunswick, N.J.) modified for high temperature operation and containing silicone fluid (Dow Corning Corp., Midland, Mich.). Approximately 10 ml of a late log phase culture (about 8 hours old) was used to inoculate the reactor, which contained 750 ml of medium and 10 g/l elemental sulfur. The reactor was purged with prepurified $N_2$ at a rate of 50 ml/min to ensure anaerobic conditions and mix the vessel contents (no additional agitation was supplied). Continuous operation was initiated during late log phase, and the working volume of the reactor was maintained at 750 ml. Feed rate changes were made in the direction of increasing dilution rate, and minimum of three reactor volume changes were allowed after each adjustment for the system to reach steady state. An additional 2.0 grams of sulfur were added to the reactor after every other dilution rate increase to ensure that an excess of sulfur was always present. In general, the sulfur remained in the reactor and little, if any, was carried out in the effluent.

Bacterial growth was followed by direct cell counts using epifluorescence microscopy with acridine orange stain. The production of $H_2S$ and $CO_2$ was measured using a Varian 3700 gas chromatograph (VarianAssoc., Sunnyvale, Calif.) with a 6 foot by ⅛ inch HayeSep-N column (Alltech Assoc., Deerfield, Ill.) and a thermal conductivity detector. The production of $H_2$ could not be qualified, due to interference from the $N_2$ purge. A Standard 286/10 microcomputer (CompuAdd Corp., Houston, Tex.) with a DAS-16 A/D interface (Metrabyte Corp., Taunton, Mass.) was used for data acquisition and peak integration.

The most significant result from this early work is that cell densities approaching batch maxima can be achieved at relatively high dilution rates. Considering that these maximal cell densities are low in comparison with most mesophiles, it is apparent that the most efficient strategy for generating large amounts of *P. furiosus* biomass for production of enzymes will involve operating relatively small continuous reactors at high volumetric efficiencies.

EXAMPLE 2

Cell-free Saccharification Enzyme Preparation Obtainable from *P. furiosus*

Growth of cells. *P. furiosus* was grown in artificial sea water supplemented with 10 g/l elemental sulfur and carbohydrate substrate, typically 3 g/l of soluble starch, unless otherwise specified, as described in Example 1. For the present studies, typically one liter bottles were inoculated with ~20 ml of a late log phase culture and incubated for ~12 hours at 98° C. in a silicon oil bath. Sulfur was removed by filtration and the cell pellet was recovered by centrifugation at about 12,000×g for 30 minutes.

Intracellular enzyme preparation. Cell pellets were resuspended in 0.1 M sodium phosphate buffer (pH 7.0) and sonicated while on ice for a total of two minutes with pulses at 30 sec intervals at a 50% duty cycle in a Tekmar Sonic Disrupter Model 300. The sonicated cells were centrifuged at about 18,000×g for 30 minutes to remove remaining sulfur and cell debris. The supernatant from this step was dialyzed overnight at 4 C. against 0.1 M sodium phosphate buffer (pH 7.0) containing 0.01% sodium azide.

Extracellular enzyme preparation. For extracellular enzyme activities, supernatants from the original centrifugation (i.e., the culture media) were concentrated from 1 liter to about 5 ml using, in succession, a Millipore Minitan ultrafiltration unit with a 10,000 molecular-weight-cutoff membrane, and a Novacell stirred cell with a 10,000 molecular-weight-cutoff membrane. These samples were dialyzed overnight at 4° C. against 0.05 M N-(2-hydroxyethyl)-N'-3-propanesulfonic acid (EPPS) buffer (pH 7.0) and 0.01% sodium azide. EPPS was used instead of phosphate to prevent precipitation of salts from the media.

Amylase, pullulanase and glucosidase assays. 0.5 ml of 2% soluble starch (autoclaved), for amylase assay, or pullulan, for pullulanase, was added to 0.5 ml of 0.1 M sodium acetate-acetic acid buffer, pH 5.6. 10–100 µl of enzyme preparation, as described above, was added; and samples were incubated at 98° C. for 30 minutes; the reaction was stopped by cooling on ice. The amount of reducing sugar released was determined using the dinitrosalicylic acid method (Barnfeld, P., 1955, Methods in Enzymology 1:149–50). One unit of enzyme activity was defined as the amount of enzyme that released one nmol of reducing sugar (as a glucose standard) per minute under the assay conditions used.

α-Glucosidase was assayed using p-nitrophenyl-α-D-glucopyranoside (PNP-α-G) as substrate, and β-glucosidase was assayed using p-nitrophenyl-β-D-glucopyranoside (PNP-β-G) as substrate. Assays were conducted as follows; for each assay, 1.0 ml of substrate consisting of 10 mM PNP-α-G or PNP-β-G in 0.1 M sodium phosphate buffer, pH 5.5, was pipetted into a quartz cuvette. The cuvettes were inserted into a heated cell holder and preincubated for 5 to 10 minutes at the assay temperature of 98° C. Following the preincubation, enzyme sample (10 µl) was added to the cuvette and the evolution of p-nitrophenol (PNP) was followed by monitoring $A_{405}$. One unit of glucosidase activity was that amount of enzyme releasing one µmol PNP per minute under the standard conditions, from the appropriate α or β substrate.

pH Optima. To determine pH optima of the various enzyme activities, the protocols above were used with the substitution of the appropriate buffer. For pH values of 4.0 to 5.6, 0.1 M sodium acetate-acetic acid buffer was used, while from pH 5.7 to 8.0, 0.1 M sodium phosphate buffer was used. Temperature optima were determined by performing the appropriate assay at the temperature indicated in a stoppered cuvette. Temperature and pH optima were determined using cell extract samples prepared as described above.

EXAMPLE 3

Purification and Characterization of α-glucosidase and β-glucosidase from *Pyrococcus furiosus*

This example discusses the purification of -glucosidase from *P. furiosus* in detail, and characterization of this enzyme and the β-glucosidase of the present invention. Unless otherwise stated, all steps were conducted at room temperature. Sodium phosphate buffers were prepared from monobasic and dibasic salts according to Gomori, G., 1959, Methods Enzymol. 1:138–146, to ensure proper pH. All buffers were titrated to the desired pH at room temperature.

Cell cultivation and harvesting. Culture medium was identical to that used in Example 1, except it was supplemented with 1 g/l yeast extract, 2 g/l tryptone, and 3 g/l soluble starch. The fermentation flask had a total volume of 3 l and a working volume of 1.5 l and was kept at 98 C. Cells were grown in batch mode until mid log phase and then switched to continuous mode with a dilution rate of about 0.5 $hr^{-1}$. Cell densities, monitored by epifluorescence microscopy with acridine orange stain (Hobbie, J. E., Daley, R. J., and Jasper, S., 1977, Appl. Environ. Microbiol. 33:1225–1228), averaged about 0.8–1.4×$10^8$ cells/ml. A total of 80 liters of cells were grown and subsequently harvested by centrifugation at about 10,000×g for 20 minutes. The final wet weight of *P. furiosus* cell paste was 37.6 g or 0.47 g per liter of culture. Cell pellets were frozen at −20° C. until use.

Cell disruption. Cell paste was resuspended in about 50 ml of 0.1 M sodium phosphate, pH 7.3. After vortexing, the resuspended cells were sonicated in 10 ml portions for a total of 2 minutes in a Tekmar Sonic Disrupter model TM300 working at 50% duty cycle. The resuspension was kept in an ice bath to ensure it did not heat significantly during sonication. Following sonication, the resuspension was centrifuged at 15,000×g for 30 minutes. The resultant supernatant was collected and the pellet consisting of sulfur and cell debris had no α-glucosidase activity and was discarded.

Ammonium sulfate precipitation. Solid ammonium sulfate was added to the supernatant from above to a final concentration of 176 g/l (30% saturation at room temperature) and stirred for 2 hours. The solution was then centrifuged at 15,000×g for 30 minutes. The volume of the supernatant fluid was measured and brought to 70% saturation by and additional 273 g/l ammonium sulfate, stirred for 2 hours and then centrifuged at 15,000×g for 30 minutes. The pellet was then resuspended in 20 mM Tris-HCl, pH 8.5 and dialyzed against this buffer for 4 hours.

Anion exchange chromatography. The sample was applied in about 25 ml portions in two separate runs to a DEAE-Cellulose (DE52) column (2 by 30 cm) equilibrated with 20 mM Tris-HCl pH 8.5. The α-glucosidase activity was eluted from the column with a linear gradient of 240 ml total volume from 0 to 400 mM NaCl in 20 mM Tris-HCl. Fractions of 60 drops/tube (about 2.4 ml/tube) were collected and monitored for OD 280 ($A_{280}$), α-glucosidase activity and conductivity (to calculate theoretical NaCl concentration) as shown in FIG. 4. Fractions containing activity were pooled (total volume from both runs was 108 ml) and concentrated in a Filtron Technology Corporation Novacell Stirred Cell with 10 kDa MWC under 40 psi pressure. The retentate (about 10 ml) was dialyzed overnight against 0.1 M sodium phosphate pH 7.0, 0.1 g/l sodium azide.

Fractions from this anion exchange chromatography were also assayed for the activity of β-glucosidase under the standard conditions. The bulk of this activity was found in the leading peak of $A_{280}$ where little α-glucosidase activity was detected. However, some additional activity of β-glucosidase was retained on the anion exchange column and was eluted by the NaCl gradient, but not as a distinct peak.

Chromatography on hydroxyapatite. The concentrated α-glucosidase sample was applied to a hydroxyapatite column (2 by 20 cm) equilibrated with 0.1 M sodium phosphate, pH 7.0. The α-glucosidase activity was eluted with a linear gradient of sodium phosphate from 0.1 M to 0.5 M (240 ml total volume). Fractions of about 2.4 ml/tube were collected and monitored for OD 280, α-glucosidase activity and conductivity. Fractions containing activity were pooled (total volume 36 ml), concentrated to about 10 ml in the Novacell Stirred Cell and further concentrated to about 0.5 ml by successive centrifugation (total time of about 1 hr) in the Amicon Microconcentrators.

Analytical electrophoresis. SDS-polyacrylamide gel electrophoresis was accomplished using the discontinuous system of Laemmli. For determination of molecular weight, protein standards (Bio Rad) were run with parallel lanes. Protein bands were visualized either by silver stain (Bio Rad Silver Stain Kit) or by 0.1% Coomassie Brilliant Blue R. Rf values were calculated relative to the bromphenol-blue tracking dye. α-Glucosidase activity was measured within the gel by incubating the gel in 1% Triton X-100 for 30 minutes followed by incubation in 10 mM PNP-α-G for 30 minutes. The gel was then incubated 70° C. for about until a yellow band was visualized.

Native polyacrylamide gel electrophoresis was conducted in the same manner as above except for the elimination of SDS. Proteins were visualized by silver stain procedure as above and α-glucosidase activity was detected similarly, except the Triton X-100 incubation was eliminated. β-glucosidase was detected by the same method, except that the substrate was PNP-β-G.

Preparative electrophoresis and electroelution. Native (non-dissociating, discontinuous) polyacrylamide gel electrophoresis of the concentrated pool containing α-glucosidase activity, and detection of activity within the gel, was performed as described under electrophoresis. The activity band was cut from the gel, and placed in a dialysis bag lengthwise with about 5 ml of native polyacrylamide gel running buffer (3.0 g/l Tris and 14.4 g/l glycine, pH 8.3). Electroelution was accomplished by placing the dialysis bag containing the gel slice and buffer in a horizontal electrophoresis system for submerged gel electrophoresis (BRL Model H5). Running buffer was the same as for the native polyacrylamide gel electrophoresis. The horizontal unit was run at 25 mA for about 12 hr. Following electroelution, the fluid was removed from the dialysis bag and dialyzed against 0.1 M sodium phosphate, pH 6.8.

Purification results. The purification factor and yield at each step of the purification process are summarized in Table 2, below:

TABLE 2

Summary of purification of α-glucosidase from *Pyrococcus furiosus*.

| Fraction | Volume (ml) | Activity (U/ml) | Protein (mg/ml) | Specific Activity (U/mg) | Fold Purification | % Yield |
|---|---|---|---|---|---|---|
| Crude | 50 | 15.1 | 19.3 | 0.782 | 1.0 | 100 |
| Ammonium Sulfate | 50 | 12.6 | 13.3 | 0.950 | 1.2 | 84 |
| Anion Exchange | 108 | 2.83 | 0.508 | 5.58 | 7.2 | 41 |
| Hydroxyapatite | 36 | 5.78 | 0.270 | 21.4 | 27 | 28 |
| Gel filtration | 36 | 4.61 | 0.0772 | 59.9 | 77 | 22 |
| Electrophoresis | 4.1 | 15.6 | 0.0638 | 245 | 310 | 8.5 |

Substrate specificity. The substrate specificity of the purified α-glucosidase was tested with a variety of natural and synthetic glucosides. The results of kinetic assays, in terms of the Michaelis-Menten constant ($K_m$, the substrate concentration at half maximal reaction velocity) and maximum rate ($V_m$, obtained with substrate concentration in great excess over $K_m$) are summarized in Table 3, below:

TABLE 3

Hydrolysis of various glucosides by *P. furiosus* α-glucosidase.

| Substrate | $K_m$ (mM) | $V_m$ (U/mg) |
|---|---|---|
| p-Nitrophenyl-α-D-glucopyranoside | 0.26 | 287 |
| Methyl-α-D-glucopyranoside | 0.77 | 186 |
| Maltose | 5.2 | 1760 |
| Isomaltose | 8.2 | 951 |
| p-Nitrophenyl-β-D-glucopyranoside | t | — |
| Sucrose | nd | — |
| Starch | nd | — | t Only a trace of activity could be detected (i.e., ~3% of the level found with p-Nitrophenyl-α-D-glucopyranoside).
nd No activity detected (<3% of p-Nitrophenyl-α-D-glucopyranoside)

These results illustrate that this enzyme exhibits a marked preference for α-D-glucosides over the corresponding β linkage and that the (1,6) linkage between glucose residues in maltose is the preferred natural substrate of those tested.

Resistance to denaturing agents. The α-glucosidase also exhibited resistance to denaturing agents and inhibitors, including the potent ionic detergent, sodium dodecyl sulphate (SDS). Several denaturing agents were added to p-nitrophenyl-α-D-glucopyranoside, both in the presence and absence of the α-glucosidase, to control for possible degradation of the substrate in the presence of the agents. The resulting percentages of original activity observed in each case under the standard assay conditions are summarized in Table 4, below:

TABLE 4

Effects of denaturing agents and inhibitors on purified *P. furiosus* α-glucosidase.

| Inhibitor | Concentration | Activity Remaining (%) |
|---|---|---|
| Sodium dodecyl sulphate | 1% (w/v) | 22 |
| Urea | 1.0 M | 84 |
| Guanidinium hydrochloride | 1.0 M | <1 |
| Dithiothreitol | 100 mM | 83 |
| EDTA | 20 mM | 50 |
| EGTA | 20 μM | 85 |

The α-glucosidase exhibited substantial resistance to denaturation by SDS and urea during assay at 98° C., but lost all detectable activity in 1 M guanidinium hydrochloride (Table 4). The stability of this enzyme in such strong denaturing agents should facilitate its purification and its use in treatment of relatively crude materials which require solubilization and are not adversely affected by detergents.

The disulfide bond reducing agent, dithiothreitol (DTT) had only a minor effect on α-glucosidase activity at 100 mM (Table 4). Therefore, it is unlikely that disulfide bonding is important in maintaining the activity of the purified α-glucosidase.

The sensitivity of the purified α-glucosidase to metal ion chelating agents was also tested to see if such ions are required for activity, either in the active site or elsewhere. Ethylenediaminetetraacetic acid (EDTA) and [Ethylenebis(oxyethylenenitrilo)]tetraacetic acid (EGTA) were both found to partially inhibit the enzyme at 20 mM (Table 4). It is unclear why there is not complete inhibition at this concentration of these chelators.

For purposes of completing the background description and present disclosure, each of the published articles, patents and patent applications heretofore identified in this specification are hereby incorporated by reference into the specification.

The foregoing invention has been described in some detail for purposes of clarity and understanding. It will be obvious to one of ordinary skill in t he art that various combinations in form and detail can be made without departing from the scope of this invention.

What is claimed is:

1. A purified α-glucosidase obtained from *Pyrococcus furiosus* that acts on the following substrates at 95° C. and pH 5.6, in descending order of relative activity, as follows: isomaltase, maltose, methyl-α-D-glucopyranoside, and p-nitrophenol-α-D glucopyranoside.

2. The purified α-glucosidase according to claim 1 further having a pH optimum between about pH 5.2 and pH 5.8 at 98° C., and showing no significant loss of α-glucosidase activity during assay at pH 5.6 over the temperature range of 105° C. to 115° C.

3. The purified α-glucosidase according to claim 1 having an approximate molecular mass value of about 125 kilodaltons (kDa), as measured by SDS-polyacrylamide gel electrophoresis.

* * * * *